US010813872B2

(12) United States Patent
Rubin et al.

(10) Patent No.: US 10,813,872 B2
(45) Date of Patent: *Oct. 27, 2020

(54) HAIR AND SCALP FORMULATIONS

(71) Applicant: CLARITY COSMETICS INC., Potomac, MD (US)

(72) Inventors: Iris Rubin, Potomac, MD (US); Gregory Maged, Bethesda, MD (US); John Garruto, Encinitas, CA (US); Bethany McCarver, Oceanside, CA (US)

(73) Assignee: CLARITY COSMETICS INC., Potomac, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/739,774

(22) Filed: Jan. 10, 2020

(65) Prior Publication Data
US 2020/0146964 A1    May 14, 2020

Related U.S. Application Data

(63) Continuation of application No. 16/192,676, filed on Nov. 15, 2018, which is a continuation of application No. 15/957,238, filed on Apr. 19, 2018, now Pat. No. 10,159,637, which is a continuation of application No. 15/618,420, filed on Jun. 9, 2017, now Pat. No. 9,949,915.

(60) Provisional application No. 62/348,510, filed on Jun. 10, 2016.

(51) Int. Cl.
| | |
|---|---|
| A61K 8/73 | (2006.01) |
| A61K 8/42 | (2006.01) |
| A61Q 5/06 | (2006.01) |
| A61K 8/81 | (2006.01) |
| A61K 8/31 | (2006.01) |
| A61K 8/34 | (2006.01) |
| A61K 8/365 | (2006.01) |
| A61K 8/37 | (2006.01) |
| A61K 8/41 | (2006.01) |
| A61K 8/46 | (2006.01) |
| A61Q 5/02 | (2006.01) |
| A61Q 5/12 | (2006.01) |

(52) U.S. Cl.
CPC ............... *A61K 8/737* (2013.01); *A61K 8/31* (2013.01); *A61K 8/34* (2013.01); *A61K 8/342* (2013.01); *A61K 8/345* (2013.01); *A61K 8/347* (2013.01); *A61K 8/365* (2013.01); *A61K 8/37* (2013.01); *A61K 8/41* (2013.01); *A61K 8/416* (2013.01); *A61K 8/42* (2013.01); *A61K 8/463* (2013.01); *A61K 8/817* (2013.01); *A61K 8/8141* (2013.01); *A61K 8/8152* (2013.01); *A61Q 5/02* (2013.01); *A61Q 5/06* (2013.01); *A61Q 5/12* (2013.01); *A61K 2800/30* (2013.01)

(58) Field of Classification Search
None
See application file for complete search history.

(56) References Cited

U.S. PATENT DOCUMENTS

| | | |
|---|---|---|
| 5,306,489 A | 4/1994 | Goldberg |
| 5,759,527 A | 6/1998 | Patel et al. |
| 5,863,546 A | 1/1999 | Swinehart |
| 6,113,891 A | 9/2000 | Burdick et al. |
| 6,165,493 A | 12/2000 | Neurath et al. |
| 6,193,986 B1 | 2/2001 | Sakurada |
| 6,268,355 B1 | 7/2001 | Mizobuchi et al. |
| 6,281,236 B1 | 8/2001 | Farber |
| 6,312,675 B1 | 11/2001 | Deane |
| 6,350,432 B1 | 2/2002 | Modi |
| 6,375,975 B1 | 4/2002 | Modi |
| 6,406,708 B1 | 6/2002 | Karnerud et al. |
| 6,436,367 B1 | 8/2002 | Modi |
| 6,444,213 B1 | 9/2002 | Morita et al. |
| 6,471,954 B2 | 10/2002 | Christensen |
| 6,492,326 B1 | 12/2002 | Robinson et al. |
| 6,649,151 B2 | 11/2003 | Barone et al. |
| 6,673,861 B2 | 1/2004 | Tabacchi et al. |
| 6,699,464 B1 | 3/2004 | Popp et al. |
| 6,723,309 B1 | 4/2004 | Deane |
| 6,723,689 B1 | 4/2004 | Hoang et al. |
| 6,896,897 B2 | 5/2005 | Farber |
| 6,923,954 B2 | 8/2005 | Doi et al. |
| 7,078,050 B2 | 7/2006 | Fusco |
| 7,182,939 B2 | 2/2007 | Tajima et al. |

(Continued)

FOREIGN PATENT DOCUMENTS

| | | |
|---|---|---|
| EP | 1097695 B1 | 9/2002 |
| EP | 1140019 B1 | 6/2003 |

(Continued)

OTHER PUBLICATIONS

A. Leone, A. Spada, A. Battezzati, A. Schiraldi, J. Aristil, S. Bertoli. "Moringa oleifera Seeds and Oil: Characteristics and Uses for Human Health." International Journal of Molecular Sciences, vol. 17, pp. 1-14, published Dec. 20, 2016. (Year: 2016).*

(Continued)

*Primary Examiner* — Isaac Shomer
(74) *Attorney, Agent, or Firm* — Knobbe, Martens, Olson & Bear LLP

(57) ABSTRACT

Formulation to treat the scalp and/or hair are provided herein. For example, formulations for reducing inflammation of hair follicles are provided, which, in turn, in some aspects, can help facilitate hair strengthening, smoothness and/or shine.

23 Claims, No Drawings

(56) References Cited

U.S. PATENT DOCUMENTS

| | | |
|---|---|---|
| 7,247,173 B2 | 7/2007 | Kleen et al. |
| 7,262,180 B2 | 8/2007 | Mastrodonato et al. |
| 7,294,153 B2 | 11/2007 | Kleen et al. |
| 7,297,717 B2 | 11/2007 | Iwai et al. |
| 7,314,634 B2 | 1/2008 | Hernandez et al. |
| 7,326,410 B2 | 2/2008 | Doi et al. |
| 7,393,630 B2 | 7/2008 | O'Hagan et al. |
| 7,427,407 B2 | 9/2008 | Kume et al. |
| 7,459,166 B2 | 12/2008 | Golz-Berner et al. |
| 7,691,792 B1 | 4/2010 | Fisher et al. |
| 7,744,856 B2 | 6/2010 | DeFilippi et al. |
| 7,759,332 B2 | 7/2010 | Xu |
| 7,763,180 B2 | 7/2010 | Tanaka et al. |
| 7,807,188 B2 | 10/2010 | Hoath et al. |
| 7,825,207 B2 | 11/2010 | Ferenz et al. |
| 7,829,067 B2 | 11/2010 | D'Amelio, Sr. et al. |
| 7,832,413 B2 | 11/2010 | Walters et al. |
| 7,845,360 B2 | 12/2010 | Walters et al. |
| 7,858,840 B2 | 12/2010 | Hisanaka |
| 7,883,729 B2 | 2/2011 | Kohler et al. |
| 7,901,465 B2 | 3/2011 | Chiba et al. |
| 7,906,557 B2 | 3/2011 | Nishikawa et al. |
| 7,956,025 B2 | 6/2011 | Copete Vidal et al. |
| 7,959,905 B2 | 6/2011 | Axelrod et al. |
| 7,959,935 B2 | 6/2011 | Hoath et al. |
| 8,021,674 B2 | 9/2011 | Mateu et al. |
| 8,088,176 B2 | 1/2012 | DeGeorge et al. |
| 8,092,813 B1 | 1/2012 | Novicki |
| 8,114,475 B2 | 2/2012 | Thomas |
| 8,173,143 B2 | 5/2012 | Tecco et al. |
| 8,183,232 B2 | 5/2012 | Inamoto et al. |
| 8,206,749 B1 | 6/2012 | O'Hagan et al. |
| 8,241,681 B2 | 8/2012 | Herrmann et al. |
| 8,242,169 B2 | 8/2012 | Yoneda et al. |
| 8,252,298 B2 | 8/2012 | Maderazzo et al. |
| 8,309,109 B2 | 11/2012 | Tajima et al. |
| 8,309,143 B2 | 11/2012 | Campbell et al. |
| 8,337,870 B2 | 12/2012 | Kulesza |
| 8,361,520 B2 | 1/2013 | Palmer |
| 8,366,688 B2 | 2/2013 | Pesso |
| 8,372,383 B2 | 2/2013 | Dascalu |
| 8,476,316 B2 | 7/2013 | St Laurent |
| 8,506,938 B2 | 8/2013 | Lin |
| 8,518,424 B2 | 8/2013 | Sasaki et al. |
| 8,529,925 B2 | 9/2013 | Alexiades-Armenakas |
| 8,562,943 B2 | 10/2013 | Klein |
| 8,586,111 B2 | 11/2013 | Garris |
| 8,586,814 B2 | 11/2013 | Fisher et al. |
| 8,617,579 B2 | 12/2013 | Liu et al. |
| 8,623,330 B2 | 1/2014 | Gurge et al. |
| 8,628,786 B2 | 1/2014 | Novicki |
| 8,642,659 B2 | 2/2014 | Springer et al. |
| 8,697,043 B1 | 4/2014 | Ter-Antonyan et al. |
| 8,703,095 B2 | 4/2014 | Klucker et al. |
| 8,765,158 B2 | 7/2014 | Fukui et al. |
| 8,808,759 B1 | 8/2014 | Barnes et al. |
| 8,871,190 B2 | 10/2014 | Marshall et al. |
| 8,906,349 B2 | 12/2014 | Schaeffer-Korbylo et al. |
| 8,911,774 B2 | 12/2014 | Giampapa |
| 8,957,112 B2 | 2/2015 | Mallard et al. |
| 9,056,065 B1 | 6/2015 | Green-Tucker |
| 9,101,554 B2 | 8/2015 | Sakuma |
| 9,119,974 B2 | 9/2015 | Al-Qahtani |
| 9,155,915 B2 | 10/2015 | Kunin |
| 9,167,839 B1 | 10/2015 | Bezzek |
| 9,180,074 B2 | 11/2015 | Fukui et al. |
| 9,271,956 B2 | 3/2016 | Auclair |
| 9,289,495 B2 | 3/2016 | Fossel |
| 9,295,622 B2 | 3/2016 | Castro |
| 9,295,632 B1 | 3/2016 | Benn et al. |
| 9,303,231 B2 | 4/2016 | Patinier et al. |
| 9,320,744 B2 | 4/2016 | Riepl |
| 9,327,021 B2 | 5/2016 | Gallichan et al. |
| 9,346,722 B2 | 5/2016 | Looten et al. |
| 9,370,570 B2 | 6/2016 | Novicki |
| 9,399,009 B1 | 7/2016 | Clark et al. |
| 9,433,564 B2 | 9/2016 | Choi et al. |
| 9,446,089 B1 | 9/2016 | Henderson |
| 9,463,158 B2 | 10/2016 | Fossel |
| 9,480,634 B2 | 11/2016 | Das et al. |
| 9,498,420 B2 | 11/2016 | Laughlin, II et al. |
| 9,504,659 B2 | 11/2016 | Klucker et al. |
| 9,526,681 B2 | 12/2016 | Santarpia, III et al. |
| 9,532,969 B2 | 1/2017 | Silver |
| 9,539,446 B2 | 1/2017 | Schnider et al. |
| 9,642,795 B2 | 5/2017 | Kiser et al. |
| RE46,441 E | 6/2017 | Rueckl et al. |
| 9,744,231 B2 | 8/2017 | Klein |
| 9,757,317 B2 | 9/2017 | Laughlin, II et al. |
| 9,782,333 B2 | 10/2017 | Obias et al. |
| 9,789,042 B2 | 10/2017 | Sasaki et al. |
| 9,789,099 B2 | 10/2017 | Neufang et al. |
| 9,801,796 B2 | 10/2017 | Pegard |
| 9,801,900 B2 | 10/2017 | Gan et al. |
| 9,822,243 B2 | 11/2017 | Malessa et al. |
| 9,827,176 B2 | 11/2017 | Johnson |
| 9,849,071 B2 | 12/2017 | Fack et al. |
| 9,855,346 B2 | 1/2018 | Fang et al. |
| 9,949,915 B2 * | 4/2018 | Rubin ............... A61Q 5/12 |
| 10,159,637 B2 * | 12/2018 | Rubin ............... A61Q 5/12 |
| 2001/0053801 A1 | 12/2001 | Tabacchi et al. |
| 2002/0048603 A1 | 4/2002 | Burmeister et al. |
| 2002/0143063 A1 | 10/2002 | Alvarado |
| 2002/0155083 A1 | 10/2002 | Mann |
| 2002/0176876 A1 | 11/2002 | Harris et al. |
| 2003/0003069 A1 | 1/2003 | Carson et al. |
| 2003/0039619 A1 | 2/2003 | Bunger et al. |
| 2003/0093045 A1 | 5/2003 | Erdman |
| 2003/0102004 A1 | 6/2003 | Hirata |
| 2003/0113315 A1 | 6/2003 | Hirata et al. |
| 2003/0165585 A1 | 9/2003 | Mann |
| 2003/0185920 A1 | 10/2003 | Passi |
| 2004/0013618 A1 | 1/2004 | Passi |
| 2004/0057917 A1 | 3/2004 | Wolf et al. |
| 2004/0072915 A1 | 4/2004 | Rougereau et al. |
| 2004/0185016 A1 | 9/2004 | Popp et al. |
| 2004/0186042 A1 | 9/2004 | Schmaus et al. |
| 2004/0258651 A1 | 12/2004 | Pascaly et al. |
| 2004/0258652 A1 | 12/2004 | Pascaly et al. |
| 2005/0008604 A1 | 1/2005 | Schultz et al. |
| 2005/0025817 A1 | 2/2005 | Bhatia et al. |
| 2005/0025847 A1 | 2/2005 | Camus-Bablon et al. |
| 2005/0031571 A1 | 2/2005 | Khaiat et al. |
| 2005/0074474 A1 | 4/2005 | Sako |
| 2005/0089488 A1 | 4/2005 | Kim |
| 2005/0152993 A1 | 7/2005 | De Oliveira |
| 2005/0158262 A1 | 7/2005 | Parris |
| 2005/0169865 A1 | 8/2005 | Parris |
| 2005/0175646 A1 | 8/2005 | Catroux et al. |
| 2005/0220810 A1 | 10/2005 | Yano et al. |
| 2005/0226838 A1 | 10/2005 | Krause et al. |
| 2005/0249761 A1 | 11/2005 | Buenger et al. |
| 2005/0276767 A1 | 12/2005 | Blin et al. |
| 2006/0024258 A1 | 2/2006 | Fack et al. |
| 2006/0029627 A1 | 2/2006 | Tsuchida et al. |
| 2006/0051310 A1 | 3/2006 | Fack et al. |
| 2006/0051311 A1 | 3/2006 | Walter et al. |
| 2006/0057075 A1 | 3/2006 | Arkin et al. |
| 2006/0062749 A1 | 3/2006 | Shelton et al. |
| 2007/0082017 A1 | 4/2007 | Tseng |
| 2007/0082042 A1 | 4/2007 | Park et al. |
| 2007/0087744 A1 | 4/2007 | Haglund |
| 2007/0154439 A1 | 7/2007 | Dorf |
| 2007/0166241 A1 | 7/2007 | Baker |
| 2007/0243147 A1 | 10/2007 | Wolber et al. |
| 2007/0264363 A1 | 11/2007 | Bowen |
| 2007/0265353 A1 | 11/2007 | Matsuhisa |
| 2007/0286838 A1 | 12/2007 | Axelrod |
| 2007/0297992 A1 | 12/2007 | Schiemann et al. |
| 2008/0015155 A1 | 1/2008 | Mastrodonato et al. |
| 2008/0020004 A1 | 1/2008 | Birkel et al. |
| 2008/0032384 A1 | 2/2008 | Nomura |
| 2008/0057008 A1 | 3/2008 | Naden et al. |

(56) References Cited

U.S. PATENT DOCUMENTS

| | | | |
|---|---|---|---|
| 2008/0069898 A1* | 3/2008 | Smith | A61K 8/922 424/642 |
| 2008/0112898 A1 | 5/2008 | Schiemann et al. | |
| 2008/0171030 A1 | 7/2008 | Jochim et al. | |
| 2008/0175805 A1 | 7/2008 | Schlemer | |
| 2008/0175931 A1 | 7/2008 | Schlemer et al. | |
| 2008/0206371 A1 | 8/2008 | Fontaine et al. | |
| 2008/0275118 A1 | 11/2008 | Shaw et al. | |
| 2008/0305057 A1 | 12/2008 | Fox | |
| 2009/0074700 A1 | 3/2009 | Nguyen et al. | |
| 2009/0074888 A1 | 3/2009 | Bhatia et al. | |
| 2009/0098079 A1 | 4/2009 | Schiemann et al. | |
| 2009/0123398 A1* | 5/2009 | Laba | A61K 8/31 424/59 |
| 2009/0130220 A1 | 5/2009 | Johnson | |
| 2009/0170816 A1 | 7/2009 | Lacasa Mas et al. | |
| 2009/0191136 A1 | 7/2009 | Kroepke et al. | |
| 2009/0220625 A1* | 9/2009 | Herrmann | A61K 31/045 424/756 |
| 2009/0226381 A1 | 9/2009 | Maillefer et al. | |
| 2010/0008880 A1 | 1/2010 | Castro et al. | |
| 2010/0074853 A1 | 3/2010 | Gan et al. | |
| 2010/0143512 A1 | 6/2010 | Abdul-Malak et al. | |
| 2010/0227008 A1 | 9/2010 | Baker | |
| 2010/0286102 A1 | 11/2010 | Vielhaber | |
| 2011/0112041 A1 | 5/2011 | Schiffmann | |
| 2011/0244063 A1 | 10/2011 | Abdul-Malak et al. | |
| 2011/0256249 A1 | 10/2011 | Campbell | |
| 2011/0305737 A1 | 12/2011 | Alexiades-Armenakas | |
| 2012/0082629 A1 | 4/2012 | Türk | |
| 2012/0093755 A1 | 4/2012 | Humphreys | |
| 2012/0128777 A1 | 5/2012 | Keck et al. | |
| 2012/0189684 A1 | 7/2012 | Buckley et al. | |
| 2012/0201857 A1 | 8/2012 | Modi | |
| 2012/0219605 A1 | 8/2012 | Blackburn et al. | |
| 2012/0263660 A1 | 10/2012 | Altschul et al. | |
| 2012/0283233 A1 | 11/2012 | Gavin et al. | |
| 2012/0289590 A1 | 11/2012 | Ritterman et al. | |
| 2012/0316144 A1 | 12/2012 | Minobe | |
| 2012/0321684 A1 | 12/2012 | Maderazzo et al. | |
| 2013/0005774 A1 | 1/2013 | Loupenok | |
| 2013/0079395 A1 | 3/2013 | De Cupere et al. | |
| 2013/0090279 A1 | 4/2013 | Hilvert | |
| 2013/0224268 A1 | 8/2013 | Alam et al. | |
| 2013/0231317 A1 | 9/2013 | Riepl | |
| 2013/0277307 A1 | 10/2013 | Jensen et al. | |
| 2014/0004176 A1 | 1/2014 | Fossel | |
| 2014/0004177 A1 | 1/2014 | Fossel | |
| 2014/0010866 A1 | 1/2014 | Fossel | |
| 2014/0037772 A1* | 2/2014 | Lien | A61K 31/05 424/769 |
| 2014/0154200 A1 | 6/2014 | Lizarraga et al. | |
| 2014/0178478 A1 | 6/2014 | Klucker et al. | |
| 2014/0186284 A1 | 7/2014 | Sha et al. | |
| 2014/0187518 A1* | 7/2014 | Kazin | A61K 45/06 514/164 |
| 2014/0271506 A1 | 9/2014 | Laughlin, II et al. | |
| 2014/0271923 A1 | 9/2014 | Reid | |
| 2014/0271940 A1 | 9/2014 | Wurzer | |
| 2014/0271949 A1 | 9/2014 | Park et al. | |
| 2014/0294921 A1 | 10/2014 | Koverech et al. | |
| 2014/0314911 A1 | 10/2014 | Cheng | |
| 2014/0348873 A1 | 11/2014 | Banov | |
| 2014/0350269 A1 | 11/2014 | Eiji Borges Sato | |
| 2015/0064122 A1 | 3/2015 | Meyer et al. | |
| 2015/0079175 A1 | 3/2015 | Junior et al. | |
| 2015/0080265 A1 | 3/2015 | Elzinga et al. | |
| 2015/0086522 A1 | 3/2015 | Velez | |
| 2015/0139929 A1 | 5/2015 | Dixon | |
| 2015/0157542 A1 | 6/2015 | Schaeffer-Korbylo et al. | |
| 2015/0174182 A1 | 6/2015 | Agisim et al. | |
| 2015/0177221 A1 | 6/2015 | Peterson | |
| 2015/0182447 A1 | 7/2015 | Park | |
| 2015/0182448 A1 | 7/2015 | Yuan | |
| 2015/0265526 A1 | 9/2015 | Christensen | |
| 2015/0297504 A1 | 10/2015 | Botto et al. | |
| 2015/0352022 A1 | 12/2015 | Laughlin, II et al. | |
| 2015/0360183 A1 | 12/2015 | Jensen et al. | |
| 2016/0000682 A1 | 1/2016 | Brooks et al. | |
| 2016/0001099 A1 | 1/2016 | Castro et al. | |
| 2016/0008297 A1 | 1/2016 | Schmaus et al. | |
| 2016/0030553 A1 | 2/2016 | Legon | |
| 2016/0067181 A1 | 3/2016 | Sawa | |
| 2016/0081895 A1 | 3/2016 | Elliott et al. | |
| 2016/0151270 A1 | 6/2016 | Brooks et al. | |
| 2016/0175238 A1 | 6/2016 | Shin et al. | |
| 2016/0175432 A1 | 6/2016 | Ma et al. | |
| 2016/0200701 A1 | 7/2016 | Berry et al. | |
| 2016/0206573 A1 | 7/2016 | Garcines et al. | |
| 2016/0227776 A1 | 8/2016 | Kawazu et al. | |
| 2016/0250137 A1 | 9/2016 | Noor et al. | |
| 2016/0279073 A1 | 9/2016 | Donsky et al. | |
| 2016/0287484 A1 | 10/2016 | Neame | |
| 2016/0316750 A1 | 11/2016 | Gries et al. | |
| 2016/0317480 A1 | 11/2016 | Brockman | |
| 2016/0324754 A1 | 11/2016 | Cure et al. | |
| 2016/0324914 A1 | 11/2016 | Compadre et al. | |
| 2016/0330957 A1 | 11/2016 | Quiroz et al. | |
| 2016/0356798 A1 | 12/2016 | Watkins | |
| 2016/0367457 A1 | 12/2016 | Mathis et al. | |
| 2016/0374352 A1 | 12/2016 | Modak et al. | |
| 2016/0375136 A1 | 12/2016 | Gavin et al. | |
| 2017/0000707 A1 | 1/2017 | Grevalcuore et al. | |
| 2017/0014314 A1 | 1/2017 | Alexandrova | |
| 2017/0020807 A1 | 1/2017 | Lutz et al. | |
| 2017/0080084 A1 | 3/2017 | Brito et al. | |
| 2017/0096418 A1 | 4/2017 | Patron | |
| 2017/0119658 A1 | 5/2017 | Turvey | |
| 2017/0128355 A1 | 5/2017 | Giampapa et al. | |
| 2017/0128522 A1 | 5/2017 | Gavaris | |
| 2017/0209383 A1 | 7/2017 | Gerchenson | |
| 2017/0216177 A1 | 8/2017 | Thrower | |
| 2017/0216368 A1 | 8/2017 | Moreno Gonzalez | |
| 2017/0231895 A1 | 8/2017 | Bae | |
| 2017/0231899 A1 | 8/2017 | Siddiqui | |
| 2017/0266096 A1 | 9/2017 | Kroon et al. | |
| 2017/0266099 A1 | 9/2017 | Kroon et al. | |
| 2017/0273899 A1 | 9/2017 | Kiser et al. | |
| 2017/0281492 A1 | 10/2017 | Dersh et al. | |
| 2017/0281526 A1 | 10/2017 | Dersh et al. | |
| 2017/0281690 A1 | 10/2017 | Moreno Gonzalez | |
| 2017/0290799 A1 | 10/2017 | Panin et al. | |
| 2017/0348203 A1 | 12/2017 | Schelges et al. | |
| 2017/0354585 A1 | 12/2017 | Rubin et al. | |
| 2017/0368376 A1 | 12/2017 | Yang et al. | |

FOREIGN PATENT DOCUMENTS

| | | | |
|---|---|---|---|
| EP | 1061799 B1 | 4/2004 | |
| EP | 0947491 B1 | 5/2004 | |
| EP | 1000603 B1 | 2/2005 | |
| EP | 1077675 B1 | 8/2005 | |
| EP | 1222915 B1 | 9/2005 | |
| EP | 0978270 B1 | 2/2006 | |
| EP | 1493423 B1 | 6/2006 | |
| EP | 1252836 B1 | 8/2006 | |
| EP | 1192934 B1 | 10/2006 | |
| EP | 1566175 B1 | 10/2006 | |
| EP | 1152022 B1 | 2/2007 | |
| EP | 1410784 B1 | 2/2007 | |
| EP | 1353645 B1 | 9/2007 | |
| EP | 1629865 B1 | 10/2008 | |
| EP | 1631245 | 1/2009 | |
| EP | 1631245 B1 * | 1/2009 | A61Q 5/02 |
| EP | 1816998 B1 | 3/2009 | |
| EP | 2090295 A1 | 8/2009 | |
| EP | 2029170 B1 | 10/2009 | |
| EP | 2218447 A1 | 8/2010 | |
| EP | 1576882 B1 | 10/2010 | |
| EP | 1116483 B1 | 12/2010 | |
| EP | 1778289 B1 | 1/2011 | |
| EP | 1014916 B2 | 6/2011 | |
| EP | 1696870 B1 | 9/2011 | |

(56) References Cited

FOREIGN PATENT DOCUMENTS

| | | |
|---|---|---|
| EP | 1937366 B1 | 12/2011 |
| EP | 1581052 B1 | 6/2012 |
| EP | 1693050 B1 | 7/2012 |
| EP | 2120845 B1 | 10/2012 |
| EP | 1370241 B1 | 11/2012 |
| EP | 1545499 B1 | 2/2013 |
| EP | 2214631 B1 | 4/2013 |
| EP | 1627667 B2 | 5/2013 |
| EP | 2649986 A2 | 10/2013 |
| EP | 2650356 A1 | 10/2013 |
| EP | 2662074 A1 | 11/2013 |
| EP | 2145946 B1 | 1/2014 |
| EP | 2155888 B1 | 7/2014 |
| EP | 2179047 B1 | 1/2015 |
| EP | 2839833 A1 | 2/2015 |
| EP | 2842607 A1 | 3/2015 |
| EP | 2529726 B1 | 6/2015 |
| EP | 2878304 A1 | 6/2015 |
| EP | 2700413 B1 | 10/2015 |
| EP | 2065030 B1 | 11/2015 |
| EP | 2977044 A1 | 1/2016 |
| EP | 2464328 B1 | 3/2016 |
| EP | 2604298 B1 | 3/2016 |
| EP | 3015 114 A1 | 5/2016 |
| EP | 3031322 A1 | 6/2016 |
| EP | 1485066 B1 | 9/2016 |
| EP | 2885004 B1 | 10/2016 |
| EP | 2090296 B1 | 3/2017 |
| EP | 3142633 A1 | 3/2017 |
| EP | 3159044 A1 | 4/2017 |
| EP | 2467120 B1 | 5/2017 |
| EP | 3174519 A1 | 6/2017 |
| EP | 2925412 B1 | 7/2017 |
| EP | 3191074 A1 | 7/2017 |
| EP | 2370052 B1 | 8/2017 |
| EP | 2774601 B1 | 8/2017 |
| EP | 2225003 B1 | 10/2017 |
| EP | 2589693 B1 | 10/2017 |
| EP | 3231414 A2 | 10/2017 |
| EP | 2392311 B1 | 11/2017 |
| EP | 2528577 B1 | 1/2018 |
| WO | WO 2005/018629 | 3/2005 |
| WO | WO 2010/023559 | 3/2010 |
| WO | WO 2010/151240 | 12/2010 |
| WO | WO 2011/056226 | 5/2011 |
| WO | WO 2011/146837 | 11/2011 |
| WO | WO 2011/162954 | 12/2011 |
| WO | WO 2012/011904 | 1/2012 |
| WO | WO 2012/077120 | 6/2012 |
| WO | WO 2012/092528 | 7/2012 |
| WO | WO 2012/109152 | 8/2012 |
| WO | WO 2013/065051 | 5/2013 |
| WO | WO 2013/139808 | 9/2013 |
| WO | WO 2013/139812 | 9/2013 |
| WO | WO 2014/027370 | 2/2014 |
| WO | WO 2014/071354 | 5/2014 |
| WO | WO 2014/076533 | 5/2014 |
| WO | WO 2014/134620 A1 | 9/2014 |
| WO | WO 2014/149867 | 9/2014 |
| WO | WO 2014/152382 | 9/2014 |
| WO | WO 2014/162280 | 10/2014 |
| WO | WO 2014/179520 | 11/2014 |
| WO | WO 2015/030702 | 3/2015 |
| WO | WO 2015/043931 | 4/2015 |
| WO | WO 2015/068052 | 5/2015 |
| WO | WO 2015/074667 | 5/2015 |
| WO | WO 2015/083174 | 6/2015 |
| WO | WO 2015/092609 | 6/2015 |
| WO | WO 2015/138479 | 9/2015 |
| WO | WO 2015/140138 | 9/2015 |
| WO | WO 2015/164290 | 10/2015 |
| WO | WO 2015/164433 A1 | 10/2015 |
| WO | WO 2015/175333 A1 | 11/2015 |
| WO | WO 2016/012110 | 1/2016 |
| WO | WO 2016/012587 | 1/2016 |
| WO | WO 2016/012757 | 1/2016 |
| WO | WO 2016/012797 | 1/2016 |
| WO | WO 2016/018315 A1 | 2/2016 |
| WO | WO 2016/040757 | 3/2016 |
| WO | WO 2016/044374 | 3/2016 |
| WO | WO 2016/112201 | 7/2016 |
| WO | WO 2016/118907 | 7/2016 |
| WO | WO 2016/138505 | 9/2016 |
| WO | WO 2016/144675 | 9/2016 |
| WO | WO 2016/178660 | 11/2016 |
| WO | WO 2016/196989 | 12/2016 |
| WO | WO 2017/034384 A1 | 3/2017 |
| WO | WO 2017/037534 | 3/2017 |
| WO | WO 2017/059136 | 4/2017 |
| WO | WO 2017/068505 | 4/2017 |
| WO | WO 2017/087924 | 5/2017 |
| WO | WO 2017/108902 A1 | 6/2017 |
| WO | WO 2017/161036 | 9/2017 |
| WO | WO 2017/161387 | 9/2017 |
| WO | WO 2017/204618 | 11/2017 |
| WO | WO 2018/000060 A1 | 1/2018 |

OTHER PUBLICATIONS

Hs Nahm. "Quality Characteristics of West African Shea Butter (*Vitellaria paradoxa*) and Approaches to Extend Shelf-life." Masters Thesis, Rutgers University, 2011. pages: title page, i-xii, and 1-121. (Year: 2011).*

Tash. "The complete List of Comedogenic Oils." Holistic Health Herbalist. Https://www.holistichealthherbalist.com/complete-list-of-comedogenic-oils/accessed May 30, 2018, pp. 1-136. (Year: 2018).*

D Jaiswal, PK Rai, A Kumar, S Mehta, G Watal. "Effect of Moringa oleifera Lam. leaves aqueous extract therapy on hyperglycemic rats." Journal of Ethnopharmacology 123 (2009) 392-396. (Year: 2009).*

U.S. Appl. No. 15/618,420, filed Jun. 9, 2017, Non-Comedogenic and Non-Acnegenic Hair and Scalp Care Formulations and Method for Use, (now U.S. Pat. No. 9,949,915), (Apr. 24, 2018).

U.S. Appl. No. 15/957,238, filed Apr. 19, 2018, Non-Comedogenic and Non-Acnegenic Hair and Scalp Care Formulations and Method for Use, (now U.S. Pat. No. 10,159,637), (Dec. 25, 2018).

U.S. Appl. No. 16/192,676, filed Nov. 15, 2018, Non-Comedogenic and Non-Acnegenic Hair and Scalp Care Formulations and Method for Use.

Notification of Transmittal of the International Search Report and the Written Opinion of the International Searching Authority dated Sep. 12, 2017, in connection with corresponding international application No. PCT/US2017/036745 (12 pgs.).

Kristin Collins Jackson, "3 Paraben and Sulfate Free Shampoos, Serums, and Body Washes to go Natural With This Summer", article in bustle.com (http://www.bustle.com/articles/28720-3-paraben-and-sulfate-free-shampoos-serums-and-body-washes-to-go-natural-with-this-summer), Jun. 20, 2014, 7 pgs.

Lily Talakoub, "Smooth hair—an acne-causing epidemic," Dermatology News, published Apr. 19, 2016, URL: http://www.mdedge.com/edermatologynews/article/108161/acne/smooth-hair-acne-causing-epidemic, 4 pgs.

Tina Ferraro, "Is Your Conditioner Causing You to Break Out?," TeenVogue, published Jul. 3, 2015, URL: http://www.teenvogue.com/story/hair-conditioner-causing-acne-breakouts, 4 pgs.

Valerie Tejeda, "Are Your Hair Products Making You Break Out?," TeenVogue, published Jul. 21, 2014, http://www.teenvogue.com/story/hair-products-cause-acne, 4 pgs.

Christa Joanna Lee, "How to Get Rid of Forehead Acne," TeenVogue, published Jul. 12, 2016, URL: http://www.teenvogue.com/story/how-to-get-rid-of-forehead-acne, 4 pgs.

Carly Cardellino, "13 Surprising Reasons You Keep Breaking Out," Cosmopolitan, published May 2, 2016, http://www.cosmopolitan.com/style-beauty/beauty/advice/a32686/surprising-things-that-cause-acne/, 12 pgs.

Lexy Lebsack, "The Annoying Reason You May Be Breaking Out," Refinery29, published Jan. 9, 2016, URL: http://www.refinery29.com/hair-products-skin-break-outs, 16 pgs.

(56) References Cited

OTHER PUBLICATIONS

Porespective, "Five Causes of Adult Acne That May Surprise You," Porespective, printed May 15, 2017, URL:https://www.porespective.com/five-causes-of-adult-acne-that-may-surprise-you/, 8 pgs.
Lauren Valenti, "The Sneaky Thing That's Making You Break Out . . . All Over," MarieClaire, published Mar. 10, 2016, http://www.marieclaire.com/beauty/news/a19207/hair-products-skin-breakouts/, 8 pgs.
Kali Borovic, "12 Hair Mistakes That Cause Acne & Sabotage Your Best Skincare Efforts," Bustle, published Mar. 5, 2016, URL: https://www.bustle.com/articles/146009-12-hair-mistakes-that-cause-acne-sabotage-your-best-skincare-efforts, 17 pgs.
Alexis C. Perkins, et al., "Acne Vulgaris in Women: Prevalence Across the Life Span," 21 J Womens Health 223-230 (Feb. 2012), URL: http://online.liebertpub.com/toc/jwh/21/2, 9 pgs.
James Q. Del Rosso, et al., "Status Report From the American Acne & Rosacea Society on Medical Management of Acne in Adult Women, Part 1: Overview, Clinical Characteristics, and Laboratory Evaluation," 96(4) Cutis 236-241, Oct. 2015, URL: http://www.cutis.com/uploads/media/media_1b35c69_CT096010236.PDF, 6 pgs.
American Academy of Dermatology, Acne: Overview, https://www.aad.org/public/diseases/acne-and-rosacea/acne visited Jun. 6, 2016, 3 pgs.
Nancy Janiczek-Dolphin, et al., "Can sebum reduction predict acne outcome?" 163(4) Br J Dermatol 683-8, Oct. 2010, URL: http//www.medscape.com/viewarticle/730258, 10 pgs.
Emil A. Tanghetti, "The Role of Inflammation in the Pathology of Acne," 6 J Clinical and Aesthetic Dermatology, 27-35, Sep. 2013, 9 pgs.
Jamese . Fulton, Jr., "Comedogenicity and irritancy of commonly used ingredients in skin care products", j. Soc. Cosmet. Chem., 40, 321-333, Nov./Dec. 1989, 13 pgs.
L Lanuza. "Sebamed Everyday Shampoo for Normal to Dry Hair and Scalp." http://www.projectvanity.com/projectvanity/2011/10/27/ sebamed-everyday-shampoo-for-normal-to-dry-hair-and-scalp.html, accessed Dec. 22, 2017, originally published Oct. 27, 2011, 8 printed pages. (Year: 2011).
HerbalLocks.com. "The Top 5 Non-Comedogenic Shampoos." http://www.herballocks.com/natural-shampoos/top-5-non-comedogenic-shampoos/, accessed by examiner on Dec. 22, 2017, 10 printed pages. (Year: 2017).
Author Unknown. Skin Reference. Comedogenic Ratings (Causes Acne). http://skinreference.com/comedogenic-ratings-causes-acne/ accessed May 31, 2018, 11 printed pages. (Year: 2018).
BASF Lipofructyl MO LS 9305 Product Info Sheet [Moringa Oil], in one page, printed on Mar. 11, 2020.
BASF Puricare POE LS 9727 Product Info Sheet [Moringa Extract], in two pages, printed on Mar. 11, 2020.
Extended European Search Report for European Application No. 17811076.3, Date of Completion of Search Jan. 30, 2020, in 11 pages.
Database GNPD [Online], MINTEL; May 12, 2009 (May 12, 2009), anonymous: Conditioner, XP055661657, retrieved from www.gnpd.com Database accession No. 1105599, abstract, ingredients; p. 2.
Database GNPD [Online], MINTEL; Nov. 25, 2008 (Nov. 25, 2008), anonymous: "Treatment Deo Conditioner" XP055661664, retrieved from www.gnpd.com Database accession No. 1012579, abstract, ingredients, p. 2.
Database GNPD [Online] MINTEL Apr. 14 2015, anonymous: "Oily-No Pore-Minimizing Elite Gel" XP055661592, retrieved from www.gnpd.com Database accession No. 3104805, abstract, ingredients; p. 2.
Database GNPD [Online] MINTEL; Dec. 20, 2011 anonymous: "Silver Clarifying Wash", XP055661596, retrieved from www.gnpd.com Database accession No. 1698667, abstract, ingredients; p. 3.
Database GNPD [Online] MINTEL; Jun. 22, 2015, anonymous: "Oil Balance Face Wash", XP055661772, retrieved from www.gnpd.com Database accession No. 3244397, abstract ingredients, p. 2.
Database GNPD [Online] MINTEL; Oct. 17, 2012, anonymous: "Pimple Clearing Face Wash", XP055661780, retrieved from www.gnpd.com Database accession No. 1900083, abstract, ingredients; p. 2.
Database GNPD [Online] MINTEL; Mar. 7, 2016, anonymous: "Special Acne Cream", XP055661608, retrieved from wwww.gnpd.com Database accession No. 3842049.

\* cited by examiner

HAIR AND SCALP FORMULATIONS

CROSS REFERENCE TO RELATED APPLICATION

This application is a continuation of U.S. patent application Ser. No. 16/192,676, filed Nov. 15, 2018, which is a continuation of U.S. patent application Ser. No. 15/957,238, filed Apr. 19, 2018, now U.S. Pat. No. 10,159,637, which is a continuation of U.S. patent application Ser. No. 15/618,420, filed Jun. 9, 2017, now issued as U.S. Pat. No. 9,949,915, which claims the benefit of Provisional U.S. Patent Application No. 62/348,510, filed Jun. 10, 2016, the entire contents and disclosure of each of which, both express and implied, is incorporated herein by reference.

BACKGROUND

When a person uses hair products on their hair, those same hair products can migrate to the skin through various mechanisms. For example, when shampooing and/or conditioning hair, the shampoo and conditioner unavoidably come into contact with the scalp, face, neck, chest, shoulders, and back, either through direct contact or as they are rinsed off and run down the skin in the shower.

Many hair care products, including rinse off products, such as shampoos and conditioners, are also designed to leave a residue even after the product is subsequently rinsed out of the hair. Leave in haircare products by design are not rinsed out and always leave a residue. This residue may be good for the hair, but can often cause problems for the skin. This residue can be deposited on the skin directly by direct contact with the skin on the scalp, and, for example, by dripping down from the hair to the face after application as well as when it runs down the person's face, neck, chest, shoulders, and/or back in the shower. This residue can also be deposited on a person's skin indirectly, when an object successively comes into contact with the person's hair, and then their skin. For example, if the person dries their hair with a towel, the residue can be transferred to other parts of their body via the towel; residue may also be transferred from a person's hair to their face from a pillowcase.

Most hair care products are developed without consideration of the impact that the product will have on the user's skin, despite the fact that contact with the skin with each use is unavoidable. Many hair care products can also build up on the skin or scalp over time, particularly if the hair care product is intended to be left in for days at a time; as a result, the hair care products may have a dramatically detrimental effect on the skin of a user. Many hair care products also contain ingredients that can trigger irritation of the skin in some users. In some cases, hair and skin treatments may also have incompatible regimens; for example, a person with parched hair strands resulting from coloration of their hair, may require hair products with significant amounts of oils and conditioning agents, some of which can be comedogenic to the skin.

According to the American Academy of Dermatology [AAD], a "comedo" is an "acne lesion", a hard blockage created from an excess of sebum combined with keratin (skin debris) in a pore which can lead to whiteheads, blackheads and pimples. Accordingly, the term, "comedogenic", refers to ingredients or products that have a tendency to block pores and promote comedones or acne.

Those with curly and/or frizzy hair may use smoothing products that traditionally contain ingredients such as oils and conditioning agents that can be comedogenic, or can become comedogenic in combination with other ingredients. For example, some common hair smoothing products, such as some silicone hair smoothing products, have not been found to be significantly comedogenic on their own, but have been found to increase the penetration of other ingredients in a formulation, which may result in a more comedogenic product. This means that hair care products can, in many cases, contribute to and exacerbate skin conditions such as acne (or "acne vulgaris"), the most common skin disease in the United States.

Acne vulgaris affects up to 50 million people in the United States alone. Acne is not just a condition that affects teenagers. Acne is highly prevalent in adult women, with one study showing that 45% of women aged 21-30, 26% aged 31-40, and 12% aged 41-50 had clinical acne. Adult acne in women is also on the rise. According to the American Academy of Dermatology (AAD), acne can contribute to depression, anxiety, and poor self-image. It can also leave permanent scars.

Acne may arise when hair follicles (pilosebaceous units) become clogged. Acne is characterized by comedones, clogged pores in the skin, which can either be open comedones ("blackheads") or closed comedones ("whiteheads"). Acne is also characterized by pimples, which can appear as inflammatory papules or pustules, cysts, or nodules.

Acne is caused by several major mechanisms: inflammation, oil/sebum, follicular hyperkeratinization, propionibacterum acnes (*P. acnes*), a bacteria, and hormones. Sebum, an oily substance secreted by the sebaceous glands of the skin, can cause dead skin cells to stick together, which can clog pores and plug hair follicles, causing acne. Sebum secretion has been correlated with acne severity, with high sebum secretion levels tended to be correlated with more severe acne; in some cases, a high sebum secretion rate may even be the decisive factor in inflammatory acne.

*P. acnes* is a bacteria that lives on the skin and can also get inside the follicle and contribute to inflammation, causing inflammatory acne lesions, including papules, cysts, and nodules. Conventional belief was that all inflammatory acne lesions arose from comedones. Recently, acne has been identified to be a primary inflammatory condition. There is evidence that inflammation plays a role at all stages of acne development, and can even be observed subclincally before the formation of comedones.

Acne can also be caused or exacerbated by certain cosmetics or styling products. "Acne cosmetica" is a form of acne that is caused by or exacerbated by the use of certain cosmetic products, including, though not limited to, makeup and sunscreen. "Acne cosmetica" typically results from a chemically-induced plugging of the hair follicles by these products. Certain cosmetic products can also produce folliculitis, or inflammation of the hair follicle, which appears as small bumps on the skin that can be skin-colored, pink, or red, having an appearance similar to acne.

For example, "pomade acne" is a similar condition to "acne cosmetica," also resulting from chemically-induced plugging of the hair follicles, and characterized by bumps on the forehead caused by oily hair care styling products. This condition was originally described primarily in African American men. Both "acne cosmetica" and "pomade acne" may also be referred to generally as "acneiform eruptions." Pomade acne has more recently been described as being an issue in all skin types, in both men and women due to hair products that smooth the hair, add shine, and reduce frizz. These products can contain oils, and waxes that clog pores, trap bacteria, and cause inflammation. Users of these products may find that these products are transferred to their pillow at night if left in their hair; as a result, users of these products may find that their faces are rolling around in oily, waxy, hair products all night. (Other hair products, particularly products not designed to be washed out within a day or so, may also cause similar problems.)

The ingredients in these hair products that clog pores and cause acne are not limited to oils and waxes used for styling and conditioning, as other ingredients can be problematic. Comedogenic or potentially comedogenic components include PVP/DMAPA acrylates, cyclopentasiloxane, panthenol, dimethicone, some silicones (typically to a mild degree), Quaternium-70, oils, and petrolatum. These ingredients may be comedogenic themselves, or, as mentioned previously, may enhance the comedogenicity, irritation, and/or allergic potential of other ingredients. For example, petrolatum itself is non-comedogenic, but is occlusive and can trap moisture and other ingredients in the hair follicles, causing stronger reactions to these ingredients.

For patients with adult acne, the AAD recommends using personal care products, including hair care products, which have one of the following labels: "non-comedogenic," "non-acnegenic," "oil-free," or "won't clog pores." However, these labels are not typically found on hair care products because hair care products are not typically formulated to be "non-comedogenic," "non-acnegenic," or "oil-free." Currently, it is not standard to test hair care products for comedogenicity or acnegenicity, or to have oil-free hair care products for acne-prone skin. In fact, there is a trend in the beauty industry to add oils to hair care products.

Many common hair care products, such as shampoos, conditioners, and other hair care products, contain oils that are or have the potential to be comedogenic. As mentioned, other products, such as silicones, can also be comedogenic in combination with other products in a formulation. Many leave-in products also contain significant quantities of these oils and silicones that can be comedogenic, including, though not limited to, styling creams, gels, pomades, hairsprays, smoothing serums, heat styling sprays, anti-frizz serums, heat-protectants, and shine sprays. Other materials in hair care products are also potentially comedogenic.

A list of comedogenic or potentially comedogenic materials includes, but is not limited to, acetylated lanolin, acetylated lanolin alcohol, algin, almond oil, apricot kernel oil, avocado oil, grapeseed oil, bismuth oxychloride, butyl stearate, carrageenan, ceteareth 20, cetyl acetate, cocoa butter, coconut oil, coal tar, hydrogenated oils, D & C Red #17, D & C Red #21, D & C Red #3, D & C Red #30, D & C Red #36, decyl oleate, disodium oleamido peg-2 sulfosuccinate, lanolin, lanolin derivatives, ethylhexyl palmitate, glyceryl stearate SE, glyceryl-3-diisostearate, hexadecyl alcohol, hydrogenated vegetable oil, isocetyl alcohol, isocetyl stearate, isodecyl oleate, isopropyl isostearate, isopropyl myristate, isopropyl palmitate, isostearyl isostearate, isostearyl neopentanoate, laureth-23, laureth-4, lauric acid, mink oil, myristic acid, myristyl lactate, myristyl myristate, octyl palmitate, octyl stearate, oleic acid, oleates, oleth-3, oleyl alcohol, olive oil, peg 200 dilaurate, PEG 8 stearate, PG monostearate, PPG 2 myristyl propionate, polyglyceryl-3-diisostearate, propylene glycol monostearate, sesame oil, sodium laureth sulfate, sodium lauryl sulfate, sorbitan oleate, soybean oil, steareth 10, stearyl heptanoate, sulfated oils, triethanolamine, wheat germ glyceride, wheat germ oil, and certain conditioning agents. Occlusive agents, including some of the above materials, can often contribute to comedogenicity and acne. See Fulton, *J. Soc. Cosmet. Chem.*, 40, 321-333 (November/December 1989) "Comedogenicity and irritancy of commonly used ingredients in skin care products" for a discussion of comedogenic materials.

In addition, most shampoos contain potentially irritating surfactants, such as sulfate-based surfactants; for example, sodium lauryl sulfate and ammonium lauryl sulfate are common surfactants that can cause irritation. Irritation to the skin can produce folliculitis and small papules on the skin, which may appear similar to acne. The folliculitis that occurs is indistinguishable from acne to the majority of hair care product users. Irritation of the follicle can also increase penetration of other materials in the hair care product into the skin follicles, increasing the potential comedogenicity and acnegenicity of many materials that could come into contact with the skin, including other materials in the hair care product formulation.

SUMMARY

Non-comedogenic and/or non-acnegenic hair care formulations may be disclosed. In some embodiments, the hair care formulation may be any kind of hair care product, including, for example, a shampoo, conditioner, or a styling product such as a styling spray, a hair spray, a shine enhancer, a root spray, a hair masque, a gel, or a styling cream, or some combination thereof. Such a formulation may allow for the cleaning, conditioning, and/or styling of the hair of a user without causing or promoting irritation or acne on the skin of the user. Such a formulation may also help resolve skin irritation, breakouts, and/or acne.

In an exemplary embodiment, the formulation may be used as part of a two-step method for washing hair. In the first step, a non-comedogenic and/or non-acnegenic shampoo is applied to cleanse the hair, and, in the second step, a non-comedogenic and/or non-acnegenic hair conditioner may be applied.

DETAILED DESCRIPTION OF THE EMBODIMENTS

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

According to an exemplary embodiment, certain hair care formulations that are non-comedogenic, or which are non-comedogenic and which do not tend to cause acne (non-acnegenic), may be disclosed. In some exemplary embodiments, such hair care formulations may prevent, improve, and/or alleviate acne, acneiform eruptions, folliculitis, pimples, blemishes, and/or skin breakouts.

According to another exemplary embodiment, methods for using the hair care formulations may be described. Such methods may be used in isolation or as part of a regimen, as may be desired. For example, in an exemplary embodiment, hair care formulations may be used in a multi-step shower method. This method may include, in step 1, applying shampoo; and, in step 2, applying conditioner. In some exemplary embodiments, hair care products may be used as part of a method for using a hair care formulation, or may be used independently, as desired. These products, or other products (such as shampoo, conditioner, and styling product) may be sold as part of a kit and designed to be compatible with or to complement one another, as may be desired.

As mentioned, a variety of causes for acne can exist, including follicular hyperkeratinization (keratinocytes stick together and block the pore), inflammation, sebum, *Propionibacterium acnes,* hormones, and other factors. Therefore, an exemplary embodiment of a non-comedogenic or non-acnegenic hair care product may include a keratinolytic agent, an anti-inflammatory agent, a sebum modulator, and/or antimicrobial agents, as well as other ingredients or additives, as desired. In some exemplary formulations, only one or more of the above components may be added; for example, in an exemplary embodiment, an anti-inflammatory agent may be added, but a keratinolytic agent, sebum modulator, or antimicrobial agent may not be added. Other combinations may also be envisioned, as desired.

According to an exemplary embodiment, a keratinolytic agent may be added to the composition, and may, for example, be used to modulate and correct abnormal follicular keratinization. This may help to prevent obstruction of the hair follicle and subsequent bacterial overgrowth. Exemplary keratinolytic agents that may be used in the formulation include willowbark (salicin) or bakuchiol. In other exemplary embodiments, as discussed above, a keratinolytic agent may not be present.

According to an exemplary embodiment, an anti-inflammatory agent may be added to the composition and may, for example, be used to reduce skin inflammation, therefore preventing and/or improving acne lesions, including comedones, papules, cysts, and nodules. Exemplary anti-inflammatory agents that may be used in the formulation include bisabolol (an anti-inflammatory chamomile derivative), stearyl glycyrrhetinate, or grapefruit seed extract (Citrus Grandis seed extract). Exemplary anti-irritant agents that may be used in the formulation include pea protein.

According to an exemplary embodiment, a sebum modulator may be added to the composition and may, for example, be used to control the amount of sebum secreted by the sebaceous glands of the skin. Clinically, measures to decrease sebum have been shown to improve acne. For example, both systemic and topical treatments may be available. An exemplary embodiment of a formulation may make use of one or more topical sebum modulators, as desired. Systemic retinoids, including isotretinoin, reduce sebum, and are one of the most powerful acne treatments available, but generally must be administered orally; as such, an exemplary embodiment of a formulation may be formulated to be compatible with a simultaneous systemic retinoid treatment or other oral or topical acne treatment of a patient, if desired. Exemplary sebum modulators that may be used in the formulation include Farnesyl Acetate, Panthenyl Triacetate, Tocopheryl Acetate, or grapefruit seed extract (Citrus Grandis seed extract). In other exemplary embodiments, as discussed above, a sebum modulator may not be present. An exemplary embodiment of a formulation may also be formulated to be compatible with a separate topical acne treatment regimen, if desired.

According to an exemplary embodiment, other ingredients or additives may be added to the formulation. These may serve a variety of purposes, or may serve multiple purposes. For example, exemplary additives may be added for the purpose of protecting against pollution or protecting against ultraviolet light (UV), or for other purposes, as may be desired. Exemplary multifunction additives that may be added to the formulation include algae extract, juice pressed from blackcurrant and raspberry leaves, butyl avocadate, zinc PCA, epilobium fleischeri extract, Laminaria Cloustoni extract, grapefruit seed extract (Citrus Grandis seed extract), or Moringa oleifera seed extract (horse-radish tree). However, in other exemplary embodiments, no multifunction additives may be added to the formulation, as may be desired.

According to an exemplary embodiment, if desired, one or more high molecular weight ingredients may be added to the formulation. For example, according to an exemplary embodiment, a large constituent such as a polymer of polyethylene glycol (PEG) may be added to the formulation. This may serve to reduce the comedogenicity of the overall formulation.

According to an exemplary embodiment, if desired, one or more of a polar sugar or a heavy metal may be added to the formulation to reduce the comedogenicity of the overall formulation. For example, according to an exemplary embodiment, zinc may be added to the formulation.

According to an exemplary embodiment, the degree of etholxylation of one or more of the molecules used in the formulation may be increased, or one or more ethoxylated materials may be added.

According to an exemplary embodiment, ingredients which are known to be comedogenic or which are potentially comedogenic, may be excluded from the formulation. For example, in an exemplary embodiment, the formulation may be oil-free, and free of laureth-4, isopropyl myristate and its analogs, lanolins, waxes, and certain conditioning agents, as well as other comedogenic or acnegenic compounds or compositions listed above or in a previous section. Occlusive agents, such as some of the above materials, can often contribute to comedogenicity and acne. In an embodiment, ingredients which are known to be irritating or potentially irritating, or ingredients that function as common allergens or which are not known to be hypoallergenic, may also be excluded from the formulation. For example, according to an exemplary embodiment, the formulation may be sulfate-free. In some embodiments, ingredients that can exacerbate the comedogenic or acnegenic properties of another ingredient but which do not themselves have significant comedogenic or acnegenic properties, such as silicone, may also be excluded. For example, in some exemplary embodiments, a silicone substitute, such as hemisqualane (a non comedogenic silicone substitute that has skin benefits) may be substituted for silicone in some quantity. In some other exemplary embodiments, silicone or another ingredient that can exacerbate the comedogenic or acnegenic effects of another ingredient may be included, and the comedogenic and acnegenic properties of the formulation may be controlled by controlling other ingredients of the formulation instead.

In an exemplary embodiment, ingredients which are known to be comedogenic or which are known to potentially be comedogenic when present in a formulation at a particular level may be kept below the level at which they are comedogenic. For example, according to an exemplary embodiment, a non-comedogenic conditioner may be provided by reducing but not eliminating the quantity of cetearyl alcohol present in a formulation; cetearyl alcohol may be comedogenic in high concentrations and minimally reactive at low concentrations.

In some embodiments, the products will also be paraben-free, formaldehyde-free, and phthalate-free, or may not have any of those components in any significant quantities.

Generally, those ingredients with a Fulton scale grade [Fulton, *J. Soc. Cosmet. Chem.*, 40, 321-333 (November/December 1989) "Comedogenicity and irritancy of commonly used ingredients in skin care products"] of greater than about 2 may be excluded from the compositions of the invention.

In an exemplary embodiment, the pH of the formulation may be controlled at a desirable level, which may serve to reduce irritation and inflammation. It may be understood that the skin of a typical person is slightly acidic, typically having a pH of around 5.5 to 6.5, whereas many soaps, particularly bar soaps, may be formulated to have a pH that is slightly basic (around 8 to 9). This may cause skin irritation and inflammation. According to an exemplary embodiment, one or more acids may be added to the formulation such that the formulation has a pH that is neutral or slightly acidic, as desired. In some exemplary embodiments, different optimal ranges may be targeted for different non-comedogenic and/or non-acnegenic hair care formulations; for example, in an exemplary embodiment, the optimal pH of the shampoo may be 5.5-6.5 and the optimal pH of the conditioner may be 4.8-5.3. In other exemplary embodiments, pH may be controlled at another level, if desired; in other exemplary embodiments, no additives may be added to the composition in order to control pH.

In another exemplary embodiment, the composition may also be formulated to have desirable qualities as a hair care product. For example, according to an exemplary embodiment, the composition may be rinseable and designed to leave only skin-friendly residue when rinsed. This may further minimize the potential for irritation or comedogenicity from the product. The rinseability of the product may also provide other benefits, such as other benefits to the skin, such as may be desired. In another exemplary embodiment, the composition may be formulated to be color-safe or may otherwise be formulated to have minimal impact on color-treated hair.

According to an exemplary embodiment, variations of the composition may be formulated for use in specialized hair care products. In an exemplary embodiment, stratification between said hair care products may be based on hair type, benefit, or intended customer. For example, according to an exemplary embodiment, variations of an exemplary composition may be prepared specifically for and marketed at women, men, teens, and others. In an exemplary embodiment, variations of an exemplary composition may be prepared specifically for curly hair, damaged hair, dry hair, fine or flat hair, as well as more typical or normal hair. In an exemplary embodiment, variations of an exemplary composition may be prepared specifically for anti-frizzing, for promoting shine, for smoothing hair, for strengthening hair, or for any other purposes as may be desired.

An exemplary formulation of a hair care product formulated to have non-comedogenic and/or non-acnegenic properties may be disclosed in table 1 and may be made by combining the following components in the proportions stated below. In an exemplary embodiment, the hair care product in table 1 may be used as a shampoo.

TABLE 1

Non-Comedogenic/Acnegenic Shampoo Exemplary Compositions

| | Ingredient | Broad % | Preferred |
|---|---|---|---|
| Part A | Water | 10.0-70.0 | 20.0-40.0 |
| | Disodium EDTA | 0.00-1.00 | 0.01-0.20 |
| Part B | Glycerin | 0.00-10.0 | 0.01-3.00 |
| | Guar Hydroxypropyltrimonium chloride | 0.05-5.00 | 0.01-0.50 |
| Part C | Citric acid | 0.00-2.00 | 0.01-1.00 |
| Part D | Phenoxyethanol | 0.01-1.00 | 0.01-1.00 |
| | Ethylhexylglycerin | 0.01-1.00 | 0.01-0.50 |
| | Polyquaternium-7 | 0.50-10.0 | 0.50-5.00 |
| | Sodium lauroyl methyl isethionate | 10.0-70.0 | 30.0-60.0 |
| | Cocamidopropylamine oxide | 1.00-20.0 | 5.00-10.0 |
| | Glycol distearate | 0.00-10.0 | 0.50-1.00 |
| Part E | Water | 0.00-8.00 | 2.00-8.00 |
| | Acrylates copolymer | 1.00-15.0 | 2.00-6.00 |
| Part F | C13-C15 alkane | 0.01-10.0 | 0.01-1.50 |
| | Bisabolol | 0.01-1.00 | 0.01-0.50 |
| | Fragrance | 0.00-3.00 | 0.01-1.00 |
| | Aminomethyl propanol | 0.01-5.00 | 0.01-1.00 |

In exemplary embodiments, the components of a chemical composition provided under a trade name may be used instead of the composition provided under the trade name. For example, according to an exemplary embodiment, an exemplary formulation of hair care product may include phenoxyethanol and ethylhexylglycerin as separate components rather than including Euxyl PE 9010. This may allow the component chemicals (such as, again, phenoxyethanol and ethylhexylglycerin) to be provided in different proportions than are found in the chemical composition provided under the trade name. The acrylates copolymer listed in table 1 may be that sold under the trade name, Carbopol Aqua SF-1; however, it will be understood by those skilled in the art that any suitable lightly cross-linked rheology modifying acrylate copolymer may be employed in the practice of the invention.

According to an exemplary embodiment, an exemplary hair care product formulation of table 1 may be prepared according to the following process or a process similar to the following. In a first step, a sanitized mixing vessel may be prepared, and a quantity of deionized water may be added to the sanitized mixing vessel. The remaining components of Part A, which in the exemplary case shown in table 2 may be Disodium EDTA, may then be mixed into the mixing vessel.

In a next step, the ingredients of part B may be premixed and may then be added to the batch. The ingredients may be mixed into the batch until the batch is uniform. The ingredients of part C may then be added to the combined batch, and again mixed until the resulting batch is completely smooth.

The combined parts A, B, and C may then be heated. For example, according to an exemplary embodiment, the combined batch may be heated to a temperature within a range of 60 to 65° C.

The ingredients of Part D may then be added. The resulting batch may be mixed until all solids are melted and the batch is uniform. Once the batch has been fully mixed, the batch may be cooled to a temperature within a range of 40 to 45° C.

Once the batch has been cooled to a temperature within a range of 40 to 45° C., the parts of part E may be added. The components of part E may be pre-mixed prior to addition, which may be done, for example, concurrently with another step preceding the addition of components in part E. Once the parts of part E have been added, the resulting batch may be mixed until uniform.

Once the resulting batch has been mixed until uniform, the ingredients of part F may be added, and likewise mixed until uniform. The batch may then be cooled to a temperature of approximately 35° C. According to an exemplary embodiment, the pH of the batch may at this time be adjusted to a pH within a range of 6.50 to 6.75.

The resulting composition may be a hair care product having the appearance of semi-viscous pearlized gel. The color may be pearlescent white to off-white, which may in some exemplary embodiments be adjusted if desired. The odor may be characteristic of the fragrance added to the composition; in some exemplary embodiments, the fragrance may be reduced or left out of the composition in order to produce an odorless composition. In an exemplary embodiment, the composition may have a pH at 25° C. of between 6.5 and 7.0, a viscosity at 25° C. (RVT), at spindle 5 at 20 rpm, of between 1000 and 12,000 cPs, and a specific gravity at 25° C. of between 0.98 and 1.03. In an exemplary embodiment, the composition may be kept to a low level of viable bacterial or fungal cells or other colony-forming units (CFU), of approximately <10 CFU/g; the composition may also be kept free of pathogens.

According to an exemplary embodiment, in a production environment, one or more small-scale batches, such as lab or pilot batches, may be made prior to large-scale manufacturing. Adjustments may be made to the production process based on, for example, the results of a batch made in a particular production environment.

Another exemplary formulation of a hair care product formulated to have non-comedogenic and/or non-acnegenic properties may be disclosed in table 2 and may be made by combining the following components in the proportions stated below. In an exemplary embodiment, the hair care product in table 2 may be used as a hair conditioner.

TABLE 2

Non-Comedogenic/Acnegenic Hair Conditioner Exemplary

| | Ingredient | Broad % | Preferred % |
|---|---|---|---|
| Part A | Water | 50.0-90.0 | 60.0-90.0 |
| | Disodium EDTA | 0.00-1.00 | 0.01-0.10 |
| | Phenoxyethanol | 0.10-5.00 | 0.75-1.25 |
| | Ethylhexylglycerin | 0.10-2.00 | 0.10-0.50 |
| | Citric acid | 0.01-1.00 | 0.01-0.50 |
| | Stearamidopropyl dimethylamine | 1.00-10.0 | 1.00-2.50 |
| | Polysorbate 80 | 0.00-5.00 | 0.10-1.00 |
| Part B | Cetearyl alcohol | 0.50-10.0 | 1.00-5.00 |
| | Behentrimonium chloride | 0.10-5.00 | 0.50-3.00 |
| | Cetyl palmitate | 0.50-5.00 | 1.00-4.00 |
| | C13-C15 alkane | 0.50-15.0 | 2.00-7.00 |
| | Shea butter cetyl esters | 0.10-8.00 | 0.50-2.00 |
| Part C | Glycerin | 0.00-10.0 | 0.10-2.00 |
| | Bisabolol | 0.01-1.00 | 0.01-0.50 |
| | Fragrance | 0.00-5.00 | 0.50-2.00 |

According to an exemplary embodiment, an exemplary hair care product formulation of table 2 may be prepared according to the following process or a process similar to the following. In a first step, a sanitized mixing vessel may be prepared, and a quantity of deionized water may be added to the sanitized mixing vessel. This DI water may then be heated to a temperature within the ranges of 80 to 85° C.

The remaining components of Part A may then be mixed into the mixing vessel. According to an exemplary embodiment, the remaining components of Part A may be added in an order or sequence, which may for example be the order in which they are shown in the table. In an exemplary embodiment, the ingredients may be added only once the previous ingredient has been fully dissolved. For example, in an exemplary embodiment, the phenoxyethanol of part A may be added, mixed until fully dissolved, and only then will the ethylhexylglycerin of part B be added.

The components of part B may be combined in a separate mixing vessel. According to an exemplary embodiment, the components of part B may be heated to a temperature in the range of 80 to 85° C. after combination, and may then be mixed until uniform.

The components of part B may then be combined with the components of part A, for example by adding the components of part B to the mixing vessel of part A. The resulting batch may then be mixed until it is smooth and uniform. The batch may then be cooled to a temperature within the range of 35 to 40° C.; according to an exemplary embodiment, mixing may be continued during this cooling process.

The ingredients of part C may then be added to the combined batch of parts A and B. According to an exemplary embodiment, ingredients may be added alone or in combination, as may be desired. The resulting batch may be mixed until uniform; following this, it may continue to be mixed and may be cooled (for example by ambient temperature) until the temperature of the batch reaches a temperature between 30 and 35° C.

The resulting composition may be a hair care product having the appearance of viscous cream. The color may be white to off-white, which may in some exemplary embodiments be adjusted if desired. The odor may be characteristic of the fragrance added to the composition; in some exemplary embodiments, the fragrance may be reduced or left out of the composition in order to produce an odorless composition. In an exemplary embodiment, the composition may have a pH at 25° C. of between 3.8 and 5.5 a viscosity at 25° C. (RVT), at spindle 5 at 20 rpm, of between 2000 and 30,000 cPs, and a specific gravity at 25° C. of between 0.98 and 1.03. In an exemplary embodiment, the composition may be kept to a low level of viable bacterial or fungal cells or other colony-forming units (CFU), of approximately <10 CFU/g; the composition may also be kept free of pathogens.

Another exemplary formulation of a hair care product formulated to have non-comedogenic and/or non-acnegenic properties may be disclosed in table 3 and may be made by combining the following components in the proportions stated below. In an exemplary embodiment, the hair care product in table 3 may be used as a curly styling cream.

TABLE 3

Non-Comedogenic/Acnegenic Curly Styling
Cream Exemplary Compositions

| | Ingredient | Broad % | Preferred % |
|---|---|---|---|
| Part A | Water | 50.0-90.0 | 75.0-85.0 |
| | Disodium EDTA | 0.00-1.00 | 0.05-0.20 |
| | Phenoxyethanol | 0.10-5.00 | 0.75-1.25 |
| | Ethylhexylglycerin | 0.10-2.00 | 0.10-0.50 |
| | Citric acid | 0.01-1.00 | 0.01-0.50 |
| | Stearamidopropyl dimethylamine | 1.00-10.0 | 1.00-2.50 |
| | Polysorbate 80 | 0.00-5.00 | 0.10-1.00 |
| Part B | Cetearyl alcohol | 0.50-10.0 | 1.00-5.00 |
| | Behentrimonium chloride | 0.10-5.00 | 0.50-3.00 |
| | Squalene | 0.00-8.00 | 0.50-5.00 |
| | C13-C15 alkane | 0.50-15.0 | 1.00-5.00 |
| | Shea butter cetyl esters | 0.10-8.00 | 0.50-5.00 |

TABLE 3-continued

Non-Comedogenic/Acnegenic Curly Styling
Cream Exemplary Compositions

|  | Ingredient | Broad % | Preferred % |
|---|---|---|---|
| Part C | Polyimide-1 | 0.00-3.00 | 0.10-1.00 |
| Part D | Puricare ™ LS9727* | 0.00-8.00 | 1.00-3.00 |
|  | Bisabolol | 0.01-1.00 | 0.01-1.00 |
|  | Hydrolyzed Pea Protein | 0.00-8.00 | 0.50-2.00 |
|  | Keratrix ™** | 0.00-10.0 | 1.50-4.50 |
|  | Fragrance | 0.00-5.00 | 0.01-2.00 |

*Includes water, glycerin, moringa Oleifera seed extract
**Includes water, glycerin, hydrolyzed ceratonia siliqua seed extract, zea mays starch, guar hydroxypropyltrimonium chloride, polyquaternium-7

According to an exemplary embodiment, an exemplary hair care product formulation of table 3 may be prepared according to the following process or a process similar to the following. In a sanitized mixing vessel, add disodium EDTA and water from Part A. Begin heating to 75-80° C. while mixing. Add remaining ingredients of Part A. Mix with heat until clear and all solids are dissolved. In a separate vessel, combine ingredients in Part B. Heat Part B to 75-80° C. and mix until uniform. Add Part B to Part A and mix until smooth and uniform. Add Part C to batch, mix until uniform and cool to 35-40° C. Add ingredients in Part D and mix until uniform. Continue mixing batch until temperate reaches 30-35° C. The product has the appearance of a white viscous cream with a pH @ 25° C.: 3.8-4.2; viscosity @ 25° C. (RVT): Spindle 5, 20 RPM 4,000-8,000 cPs; specific gravity @ 25° C.: 0.98-1.03; microbiology <10 CFU/g, No pathogens Another exemplary formulation of a hair care product formulated to have non-comedogenic and/or non-acnegenic properties may be disclosed in table 4 and may be made by combining the following components in the proportions stated below. In an exemplary embodiment, the hair care product in table 4 may be used as a blow dry styling cream.

TABLE 4

Non-Comedogenic/Acnegenic Blow Dry Styling
Cream Exemplary Compositions

|  | Ingredient | Broad % | Preferred % |
|---|---|---|---|
| Part A | Water | 50.0-90.0 | 75.0-85.0 |
|  | Disodium EDTA | 0.00-1.00 | 0.05-0.20 |
|  | Phenoxyethanol | 0.10-5.00 | 0.75-1.25 |
|  | Ethylhexylglycerin | 0.10-2.00 | 0.10-0.50 |
|  | Citric acid | 0.01-1.00 | 0.01-0.50 |
|  | Stearamidopropyl dimethylamine | 1.00-10.0 | 1.00-2.50 |
|  | Polysorbate 80 | 0.00-5.00 | 0.10-1.00 |
| Part B | Cetearyl alcohol | 1.00-5.00 | 1.00-5.00 |
|  | Behentrimonium chloride | 0.50-3.00 | 0.50-3.00 |
|  | Squalene | 0.50-5.00 | 0.50-5.00 |
|  | C13-C15 alkane | 1.00-5.00 | 1.00-5.00 |
|  | Shea butter cetyl esters | 0.50-5.00 | 0.50-5.00 |
| Part C | Puricare ™ LS9727 | 0.00-8.00 | 1.00-3.00 |
|  | Bisabolol | 0.01-1.00 | 0.01-1.00 |
|  | Hydrolyzed Pea Protein | 0.00-8.00 | 0.50-2.00 |
|  | Keratrix ™ | 0.00-10.0 | 1.50-4.50 |
|  | Fragrance | 0.00-5.00 | 0.01-2.00 |

According to an exemplary embodiment, an exemplary hair care product formulation of table 4 may be prepared according to the following process or a process similar to the following.

In a sanitized mixing vessel, add disodium EDTA and water from Part A. Begin heating to 75-80° C. while mixing. Add remaining ingredients of Part A. Mix with heat until clear and all solids are dissolved. In a separate vessel, combine ingredients in Part B. Heat Part B to 75-80° C. and mix until uniform. Add Part B to Part A and mix until smooth and uniform. Continue mixing and cool to 35-40° C. Add ingredients in Part C and mix until uniform. Continue mixing batch until temperate reaches 30-35° C. The product has the appearance of a white viscous cream with a pH @ 25° C.: 3.8-4.2; viscosity @ 25° C. (RVT): Spindle 5, 20 RPM 3,000-8,000 cPs; specific gravity @ 25° C.: 0.98-1.03; microbiology <10 CFU/g, No pathogens According to an exemplary embodiment, in a production environment, one or more small-scale batches, such as lab or pilot batches, may be made prior to large-scale manufacturing. Adjustments may be made to the production process based on, for example, the results of a batch made in a particular production environment.

Alternative compositions may also be envisioned, for example for other compositions of shampoos or conditioners or for other types of hair care products, such as styling gels or even combined shampoos and conditioners. For example, some embodiments may have relative compositions different from those shown; an exemplary composition may have a higher weight percent of one component chemical and a lower weight percent of a second component chemical. Equivalent or substantially equivalent component chemicals may also be substituted for chemicals within a composition. Appropriate substitutions may be appreciated by one of skill in the art.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A formulation for treating hair follicles, wherein the formulation comprises:
    water, wherein the water is present in an amount between 50 and 90%;
    C13-C15 alkanes, wherein the C13-C15 alkanes are present in an amount up to 15%;
    glycerin, wherein the glycerin is present in an amount in an amount up to 10%;
    bisabolol, wherein the bisabolol is present in an amount between 0.01% and 1%;
    citric acid, wherein the citric acid is present in an amount up to 2%;
    disodium EDTA, wherein the disodium EDTA is present in an amount up to 1%; and
    phenoxyethanol, wherein the phenoxyethanol is present in an amount up 5%;
    wherein the formulation excludes comedogenic elements having a Fulton scale grade greater than 2,
    wherein the formulation is fragrance free, and
    wherein the formulation reduces one or both of inflammation of hair follicles and clogging of hair follicles.

2. The formulation of claim 1, wherein the formulation excludes parabens and sulfates.

3. The formulation of claim 1, wherein the formulation further comprises ethylhexylglycerin in an amount up to 2%.

4. The formulation of claim 1, further comprising Guar hydroxypropyltrimonium chloride and polyquaternium-7.

5. The formulation of claim 1, further comprising behentrimonium chloride and cetearyl alcohol, wherein the behentrimonium chloride is present in an amount between 0.1% to 5.0%, and wherein the cetearyl alcohol is present in an amount between 0.5 to 10%.

6. The formulation of claim 1, further comprising cetearyl alcohol, wherein the cetearyl alcohol is present in an amount between 0.5% to 10.0%, behentrimonium chloride, wherein the behentrimonium chloride is present in an amount between 0.1% to 5.0% and shea butter cetyl esters.

7. The formulation of claim 1, wherein the formulation further comprises shea butter cetyl esters.

8. The formulation of claim 1, wherein the formulation further comprises shea butter cetyl esters, wherein the shea butter cetyl esters are present in an amount between 0.1 and 8.0%.

9. The formulation of claim 1, wherein the formulation further comprises ethylhexylglycerin, cetearyl alcohol, behentrimonium chloride, and shea butter cetyl esters.

10. A formulation for treating hair follicles, wherein the formulation comprises:
    water, wherein the water is present in an amount between 50 and 90%;
    C13-C15 alkanes, wherein the C13-C15 alkanes are present in an amount up to 15%;
    bisabolol, wherein the bisabolol is present in an amount between 0.01% and 1%;
    citric acid, wherein the citric acid is present in an amount up to 2%;
    disodium EDTA, wherein the disodium EDTA is present in an amount up to 1%;
    phenoxyethanol, wherein the phenoxyethanol is present in an amount up 5%,
    wherein the formulation further comprises hydrolyzed *Ceratonia siliqua* seed extract, *Zea mays* starch, and guar hydroxypropyltrimonium chloride,
    wherein the formulation excludes parabens and sulfates, and
    wherein the formulation reduces one or both of inflammation of hair follicles and clogging of hair follicles.

11. The formulation of claim 10, further comprising cetearyl alcohol, wherein the cetearyl alcohol is present in an amount between 0.5% to 10.0% and behentrimonium chloride, wherein the behentrimonium chloride is present in an amount between 0.1% to 5.0%.

12. The formulation of claim 10, wherein the formulation further comprises ethylhexylglycerin in an amount up to 2%.

13. The formulation of claim 10, wherein the formulation further comprises shea butter cetyl esters.

14. A hair and scalp care formulation, wherein the formulation comprises:
    water, wherein the water is present in an amount between 50 and 90%;
    C13-C15 alkanes, wherein the C13-C15 alkanes are present in an amount up to 15%;
    glycerin, wherein the glycerin is present in an amount in an amount up to 10%;
    phenoxyethanol, wherein the phenoxyethanol is present in an amount up 5%;
    wherein the formulation further comprises guar hydroxypropyltrimonium chloride, polyquaternium-7, ethylhexylglycerin, cocamidopropylamine oxide, acrylates copolymer, and glycol distearate;
    wherein the formulation excludes comedogenic elements having a Fulton scale grade greater than 2, and
    wherein the formulation excludes parabens and sulfates.

15. The formulation of claim 14, wherein the formulation is fragrance free, reduces irritation of hair follicles, and strengthens hair.

16. The formulation of claim 14, wherein the formulation is fragrance free.

17. The formulation of claim 14, wherein the the ethylhexylglycerin is present in an amount up to 2%.

18. The formulation of claim 14, further comprising bisabolol.

19. A formulation for treating hair follicles, wherein the formulation comprises:
    water, wherein the water is present in an amount between 50 and 90%;
    C13-C15 alkanes, wherein the C13-C15 alkanes are present in an amount up to 15%;
    bisabolol, wherein the bisabolol is present in an amount between 0.01% and 1%;
    citric acid, wherein the citric acid is present in an amount up to 2%;
    disodium EDTA, wherein the disodium EDTA is present in an amount up to 1%;
    phenoxyethanol, wherein the phenoxyethanol is present in an amount up 5%; and
    wherein the formulation further comprises a combination of a hydrolyzed *Ceratonia siliqua* seed extract, *Zea mays* starch, guar hydroxypropyltrimonium chloride, and polyquaternium-7, wherein the combination of said hydrolyzed *Ceratonia siliqua* seed extract, said *Zea mays* starch, said guar hydroxypropyltrimonium chloride, and said polyquaternium-7 is present in an amount up to 10%, and
    wherein the formulation excludes parabens and sulfates, and
    wherein the formulation reduces one or both of inflammation of hair follicles and clogging of hair follicles.

20. The formulation of claim 19, wherein the formulation is fragrance free and strengthens hair.

21. The formulation of claim 19, further comprising cetearyl alcohol, wherein the cetearyl alcohol is present in an amount between 0.5% to 10.0% and behentrimonium chloride, wherein the behentrimonium chloride is present in an amount between 0.1% to 5.0%.

22. The formulation of claim 19, wherein the formulation further comprises ethylhexylglycerin in an amount up to 2%.

23. The formulation of claim 19, wherein the formulation further comprises shea butter cetyl esters.

* * * * *